United States Patent [19]
Markus et al.

[11] Patent Number: 4,851,227
[45] Date of Patent: Jul. 25, 1989

[54] INSECTICIDAL COMPOSITION COMPRISING DIAZINON AND PROCESS FOR THE PREPARATION THEREOF

[75] Inventors: Arie Markus, Beer-Sheva; Zvi Pelah, Savyon, both of Israel

[73] Assignee: Ben-Gurion University of the Negev Research & Development Authority, Beer Sheva, Israel

[21] Appl. No.: 79,116

[22] Filed: Jul. 29, 1987

[30] Foreign Application Priority Data

Jul. 31, 1986 [IL] Israel ........................................ 79575

[51] Int. Cl.$^4$ .............................................. A61K 9/50
[52] U.S. Cl. .................................... 424/419; 424/404; 424/407; 424/408; 424/409; 424/417; 424/418
[58] Field of Search ............... 424/417, 418, 419, 408, 424/404, 407, 409

[56] References Cited

U.S. PATENT DOCUMENTS 4,107,292 8/1978 Demeth ................................ 424/78
4,670,246 6/1987 Dahl et al. ........................... 424/419

Primary Examiner—William R. Dixon, Jr.
Assistant Examiner—Jerry D. Johnson
Attorney, Agent, or Firm—Helfgott & Karas

[57] ABSTRACT

The invention provides an insecticidal composition comprising Diazinon encapsulated in microcapsules, the microcapsules having an encapsulating wall formed essentially from the reaction product of toluene diisocyanate and a polyfunctional amine, and further provides a process for encapsulating Diazinon in a microcapsular formulation comprising providing an aqueous phase containing a non-basic emulsifier, providing an organic phase containing toluene diisocyanate and Diazinon, combining the aqueous and organic phase to form an oil in water emulsion, and adding an aqueous solution of a polyfunctional amine with agitation to the emulsion, whereby the amine reacts with the toluene diisocyanate to form microcapsular envelopes about the Diazinon material.

6 Claims, No Drawings

INSECTICIDAL COMPOSITION COMPRISING DIAZINON AND PROCESS FOR THE PREPARATION THEREOF

The present invention relates to an insecticidal composition and to a process for the preparation thereof.

More particularly, the present invention relates to an insecticidal composition comprising Diazinon® as active ingredient therein and to a process for encapsulating Diazinon® in a microcapsular formulation.

Diazinon® which is phosphorothioic acid, 0,0-diethyl 0-[6-methyl-2-(1-methyethyl)-4-pyrimidinyl] ester is described and claimed in U.S. Pat. No. 2,754,243 and its insecticidal properties were first described by Gasser, Z. Naturfalsch 8b, 225 (1953).

The encapsulation of various chemical reagents. pharmaceuticals, pesticides and herbicides in general and even Diazinon® in particular, have been proposed and described in the prior art.

As described e.g. in U.S. Pat. No. 4,417,916, aqueous dispersions of pesticide and herbicide microcapsules are particularly useful in controlled release pesticidal and herbicidal formulations because they can be diluted with water or liquid fertilizer and sprayed using conventional equipment, thereby producing uniform field coverage of the pesticide or herbicide. Additives such as film forming agents can be added directly to the finished formulation to improve the adhesion of microcapsules to foliage. In some cases, reduced toxicity and extended activity of encapsulated herbicides and pesticides have been noted.

A variety of techniques have heretofore been used or proposed for encapsulation purposes. In one such process, known as "simple coacervation", a polymer separates from a solvent solution of the polymer by the action of a precipitating agent that reduces the solubility of the polymer in the solvent (e.g., a salt or a nonsolvent for the polymer). Patents describing such processes and their shell wall material include U.S. Pat. Nos. 2,800,458 (hydrophilic colloids); 3,069,370 and 3,116,216 (polymers); 3,137,631 (denatured proteins); 3,418,250 (hydrophobic thermoplastic resins); and others.

Another method involves microencapsulation based on in situ interfacial condensation polymerization. British Pat. No. 1,371,179 discloses a process which consists of dispersing an organic pesticide phase containing a polymethylene polyphenylisocyanate or toluene diisocyanate monomer into an aqueous phase. The wall forming reaction is initiated by heating the batch to an elevated temperature at which point the isocyanate monomers are hydrolyzed at the interface to form amines, which in turn react with unhydrolyzed isocyanate monomers to form the polyurea microcapsulate wall. One difficulty with this method is the possibility of continued reaction of monomer after packaging. Unless all monomer is reacted during the preparation, there will be continued hydrolysis of the isocyanate monomer with evolution of $CO_2$, resulting in the development of pressure when the formulation is packaged.

Various methods of encapsulation by interfacial condensation between direct-acting, complimentary reactions are known. Within these methods are reactions for producing various types of polymers as the capsule walls. Many of such reactions to reproduce the coating substance occur between an amine, which must be of at least difunctional character and a second reactant intermediate, which for producing a polyurea is a difunctional or polyfunctional isocyanate. The amines chiefly used or proposed in these methods are typified by ethylene diamine, having at least 2 primary amino groups. U.S. Pat. No. 3,429,827 and U.S. Pat. No. 3,577,515 are illustrative of encapsulation by interfacial condensation.

For example, U.S. Pat. No. 3,577,515 describes a continuous or batch method which requires a first reactant and a second reactant complimentary to the first reactant, with each reactant in separate phases, such that the first and second reactants react at the interface between the droplets to form encapsulated droplets. The process is applicable to a large variety of polycondensation reactions, i.e., to many different pairs of reactants capable of interfacial condensation from respective carrier liquids to yield solid film at the liquid interface. The resulting capsule skin may be produced as a polyamide, polysulfonamide, polester, polycarbonate, polyurethane, polyurea or mixtures of reactants in one or both phases so as to yield corresponding condensation copolymers. The reference describes the formation of a polyurea skin when diamines or polyamines (e.g. ethylene diamine, phenylene diamine, toluene diamine, hexamethylene diamine and the like) are present in the water phase and diiocyanates or polyisocyanates (e.g., toluene diisocyanate, hexamethylene diisocyanate and polymethylene polyphenylisocyanate) are present in the organic/oil phase. In the practice of U.S. Pat. No. 3,577,515, the liquid which preponderates becomes the continuous phase liquid. That is, in forming oil containing microcapsules, the aqueous liquid would preponderate; when water encapsulated microcapsules are formed, the oil phase would preponderate.

Of particular importance to note is that despite the general description in said patent, it specifically claims and is limited to the reaction of a polyisocyanate having at least three isocyanate groups or an isocyanate having less reactive groups in combination with another reactive intermediate such as an acyl halide, e.g., sebacoyl chloride, since a necessary condition for the reaction is the presence of at least three reactive groups.

On the other hand, U.S. Pat. No. 4,417,916 claims a process of encapsulating water-immiscible material within a shell wall of polyurea which comprises:
(a) providing an aqueous phase containing an emulsifier selected from the group consisting of sodium, potassium, magnesium, calcium or ammonium salts of lignin sulfonate;
(b) dispersing in said aqueous phase, a water-immiscible phase consisting essentially of polymethylene polyphenylisocyanate dissolved in said water-immiscible material, to form a dispersion of water-immiscible phase droplets throughout the aqueous phase;
(c) adding, with agitation, to said dispersion a polyfunctional amine, whereby said amine reacts with a polymethylene polyphenylisocyanate to form a polyurea shell wall about said water-immiscible material;

As will be noted, while said patent acknowledges and thus evidences clear awareness of the teachings of U.S. Pat. No. 3,577,515, it is limited to the use of polymethylene polyphenylisocyanate which is a large polymer, not particularly stable and quite expensive.

After further research and development it has been found that contrary to the implied teachings of U.S. Pat. No. 3,577,515, it is not necessary to carry out the reaction in the presence of a reactant having at least three isocyanate groups and contrary to the implied teachings of U.S. Pat. No. 3,577,515, polymethylene polyphenylisocyanate should not be the isocyanate of choice.

Thus, according to the present invention there is now provided a process for encapsulating Diazinon in a microcapsular formulation comprising:
(a) providing an aqueous phase containing a non-basic emulsifier;
(b) providing an organic phase containing toluene diisocyanate and Diazinon;
(c) combining said aqueous and organic phase to form an oil in water emulsion; and
(d) adding an aqueous solution of a polyfunctional amine with agitation to said emulsion, whereby said amine reacts with said toluene diisocyanate to form microcapsular envelopes about said Diazinon material.

In preferred embodiments of the present invention said process involves the additional step of:
(e) adding a suspending agent to enhance the suspension of said microcapsules in solution.

Preferably said non-basic emulsifier is selected from the group consisting of low and high density polyvinylalcohol, or Tween 20, 40 or 80 and said suspending agent is selected from the group consisting of carboxymethyl cellulose, sodium salt, Xantan gum, Karya gum and Locust bean gum.

Said polyfunctional amine can be any of the polyamines taught for this purpose in the prior art and di-, tri-, tetra- or penta-amines are especially preferred.

Thus, the invention also provides an insecticidal composition comprising Diazinon encapsulated in microcapsules, said microcapsules having an encapsulating wall formed essentially from the reaction product of toluene diisocyanate and a polyfunctional amine.

The toluene diisocyanate used in the present invention is less expensive and more readily available than polymethylene polyphenylisocyanate since it is used in the urethane industry and the process is simple without the formation of $CO_2$ or problems of separation of the encapsulated material as encountered in other prior art processes.

Furthermore, the product of the present invention is white in color and thus there is also eliminated the danger of bees confusing the microcapsules with pollen as occurs with the yellow colored products produced by U.S. Pat. No. 4,417,916 (the formulation of which is known as KNOX OUT - 2 FM).

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

(a) a first solution A was prepared by combining 800 ml $H_2O$ and 8g Tween 80;
(b) a second solution B was prepared by combining 350 ml Diazinon and 54 gr TDI;
(c) a third solution C was prepared by combining 12 gr Ethylene diamine, 10.5 gr Diethylene tri-amine and 200 ml $H_2O$.

Solution B was emulsified in solution A using mixer disperser (Ystral mixer 2000 Watts 20,000 r.p.m.). The agitation is continued until a very delicate emulsion is formed (about 10 min.).

The third emulsion solution C was gradually added with agitation. The reaction mixture is cooled all the time and this is due to the fact that the strong agitation caused the reaction mixture to heat up. The agitation is continued for an additional hour. After ½ hour 8 gr of $N_a$ bentonite (specially selected for using with insecticides and 10 gr of Carboxymethyl cellulose sodium salt are added.

EXAMPLE 2

(a) a first solution was prepared by combining 800 ml $H_2O$ and 8g polyvinylalcohol (P.V.A.);
(b) a second solution was prepared by combining 350 ml Diazinon and 54 gr TDI;
(c) a third solution was prepared by combining 12 gr Ethylene diamine, 10.5 gr Di-ethylene triamine and 200 ml $H_2O$.

The reaction was carried out as described in Example 1.

At the end between 5.5 and 6 gr of Xantan gum were added and dissolved in the reaction mixture in order to form a good and stable suspension.

EXAMPLE 3

(a) a first solution was prepared by combining 800 ml of $H_2O$ and 8 gr of polyvinylalcohol (P.V.A.);
(b) a second solution was prepared by combining 350 ml Diazinon and 54 gr TDI;
(c) a third solution was prepared by combining 23 gr ethylene diamine and 200 ml $H_2O$;

The reaction was carried out as in Example 1.

At the end 12 gr of Karya gum were added and dissolved in the reaction mixture.

EXAMPLE 4

(a) a first solution was prepared by combining 800 ml of $H_2O$ and 8 gr of polyvinylalcohol (P.V.A.);
(b) a second solution was prepared by combining 350 ml of Diazinon and 54 gr of TDI;
(c) a third solution was prepared by combining 200 ml of $H_2O$, 12 gr of Ethylene diamine and 19.2 gr Tetra ethylene penta amine;

The reaction was carried out as in Example 1.

At the end 6 gr of Xantan gum as suspending agent were added.

In all cases after adding the suspending agent the aqueous formulations received were very homogeneous.

Field tests done with the formulation of Example 2 against American cockroaches in kitchens, kindergardens, hotels, lavoratories and sewage pipes with hard and medium infestation showed that the formulation had excellent insecticidal properties.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. An insecticidal composition comprising Diazinon encapsulated in an encapsulating wall substantially free of cross linkages formed essentially from the reaction product of toluene diisocyanate and an effectively difunctional amine.

2. An insecticidal composition as defined in claim 1 wherein said effectively difunctional amine is a di or triamine.

3. A process for encapsulating Diazinon in a microcapsular formulation comprising:

(a) providing an aqueous phase containing a non-basic emulsifier;
(b) providing an organic phase containing toluene diisocyanate and Diazinon;
(c) combining said aqueous and organic phase to form an oil in water emulsion; and
(d) adding an aqueous solution of an effectively difunctional amine with agitation to said emulsion, whereby said amine reacts with said toluene diisocyanate to form microcapsular envelopes substantially free of cross linkages.

4. A process according to claim 3 comprising the additional step of:

(e) adding a suspending agent to enhance the suspension of said microcapsules in solution.

5. A process as defined in claim 3 wherein said non-basic emulsifier is selected from the group consisting of low and high density polyvinylalcohol, tween 20, tween 40 or tween 80.

6. A process according to claim 4 wherein said suspending agent is selected from Xantan gum, Karya gum and Locust bean gum.

* * * * *